US008260430B2

(12) United States Patent
James

(10) Patent No.: US 8,260,430 B2
(45) Date of Patent: Sep. 4, 2012

(54) STIMULATION CHANNEL SELECTION FOR A STIMULATING MEDICAL DEVICE

(75) Inventor: Christopher J. James, Toulouse (FR)

(73) Assignee: Cochlear Limited, Macquarie University, NSW (AU)

( * ) Notice: Subject to any disclaimer, the term of this patent is extended or adjusted under 35 U.S.C. 154(b) by 186 days.

(21) Appl. No.: 12/829,127

(22) Filed: Jul. 1, 2010

(65) Prior Publication Data

US 2012/0004705 A1    Jan. 5, 2012

(51) Int. Cl.
*A61N 1/36*    (2006.01)
(52) U.S. Cl. ............................................ 607/57; 607/55
(58) Field of Classification Search .............. 607/55–57, 607/137
See application file for complete search history.

(56) References Cited

U.S. PATENT DOCUMENTS

| | | |
|---|---|---|
| 4,114,627 A | 9/1978 | Lewyn et al. |
| 4,305,396 A | 12/1981 | Wittkampf et al. |
| 4,343,312 A | 8/1982 | Cals et al. |
| 4,373,531 A | 2/1983 | Wittkampf et al. |
| 4,532,930 A | 8/1985 | Crosby et al. |
| 4,543,956 A | 10/1985 | Herscovici |
| 4,895,152 A | 1/1990 | Callaghan et al. |
| 4,941,179 A | 7/1990 | Bergenstoff et al. |
| 5,016,280 A | 5/1991 | Engebretson |
| 5,034,918 A | 7/1991 | Jeong |
| 5,172,690 A | 12/1992 | Napphoiz et al. |
| 5,271,397 A | 12/1993 | Seligman et al. |
| 5,277,694 A | 1/1994 | Leysieffer et al. |
| 5,278,994 A | 1/1994 | Black et al. |
| 5,626,629 A | 5/1997 | Faltys et al. |
| 5,674,264 A | 10/1997 | Carter et al. |
| 5,748,651 A | 5/1998 | Sheynblat |
| 5,758,651 A | 6/1998 | Nygard et al. |
| 5,895,416 A | 4/1999 | Barreras, Sr. et al. |

(Continued)

FOREIGN PATENT DOCUMENTS

EP    0282336    9/1988

(Continued)

OTHER PUBLICATIONS

English language translation of "First Office Action," issued by the Austrian Patent Office, in connection with Austrian Patent Application No. 3B A 9165/2003-1, on Mar. 14, 2007 (2 pages).

(Continued)

*Primary Examiner* — Brian T Gedeon
(74) *Attorney, Agent, or Firm* — Kilpatrick, Townsend & Stockton, LLP.

(57) ABSTRACT

Methods and systems are disclosed for determining the stimulation channels for application of stimulation by a medical device, such as a cochlear implant or an auditory brain stimulator. In embodiments, the medical device filters a received signal to obtain a plurality of band-pass filtered signals, each corresponding to one or more stimulation channels. The medical device then selects a stimulation channel for application of stimulation based on the amplitudes of the band-pass filtered signals. The medical device determines whether to apply stimulation on the adjacent stimulation channels by determining if the amplitude of the corresponding adjacent stimulation channel exceeds an information limit. If the amplitudes for either adjacent channel fall below the information limit, the corresponding adjacent stimulation channel is eliminated from consideration. The medical device further may determine the amplitudes for application of stimulation on the adjacent stimulation channels, if selected, using a pitch steering function. This pitch steering function may specify a current level difference between the selected stimulation channel and the adjacent stimulation channel to use in applying the stimulation.

34 Claims, 10 Drawing Sheets

U.S. PATENT DOCUMENTS

| | | | |
|---|---|---|---|
| 5,963,904 | A | 10/1999 | Lee et al. |
| 6,002,966 | A | 12/1999 | Loeb et al. |
| 6,157,861 | A | 12/2000 | Faltys et al. |
| 6,205,360 | B1 | 3/2001 | Carter et al. |
| 6,289,247 | B1 | 9/2001 | Faltys et al. |
| 6,428,484 | B1 | 8/2002 | Battmer et al. |
| 6,430,402 | B1 | 8/2002 | Agahi-Kesheh |
| 6,463,328 | B1 | 10/2002 | John |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,600,955 | B1 | 7/2003 | Zierhofer |
| 6,697,674 | B2 | 2/2004 | Leysieffer |
| 6,731,767 | B1 | 5/2004 | Blamey et al. |
| 6,751,505 | B1 | 6/2004 | Van Den Honert et al. |
| 7,043,303 | B1 | 5/2006 | Overstreet |
| 7,082,332 | B2 | 7/2006 | Blamey et al. |
| 7,711,133 | B2 | 5/2010 | Goorevich et al. |
| 2001/0049466 | A1 | 12/2001 | Leysieffer et al. |
| 2002/0026091 | A1 | 2/2002 | Leysieffer |
| 2004/0098063 | A1 | 5/2004 | Goetz |
| 2005/0015133 | A1 | 1/2005 | Ibrahim et al. |
| 2005/0101878 | A1 | 5/2005 | Daly et al. |
| 2005/0107845 | A1 | 5/2005 | Wakefield et al. |
| 2005/0245991 | A1 | 11/2005 | Faltys et al. |
| 2006/0235332 | A1 | 10/2006 | Smoorenburg |
| 2007/0084995 | A1 | 4/2007 | Newton et al. |
| 2007/0255344 | A1 | 11/2007 | Van Dijik |
| 2008/0319508 | A1 | 12/2008 | Botros et al. |
| 2009/0043359 | A1 | 2/2009 | Smoorenburg |

FOREIGN PATENT DOCUMENTS

| | | |
|---|---|---|
| EP | 0836363 | 4/1998 |
| WO | 92/10134 | 6/1992 |
| WO | 93/24176 | 12/1993 |
| WO | 94/14376 | 7/1994 |
| WO | 95/01709 | 1/1995 |
| WO | 96/12383 | 4/1996 |
| WO | 97/09863 | 3/1997 |
| WO | 97/48447 | 12/1997 |
| WO | 0052963 | 9/2000 |
| WO | 00/76436 | 12/2000 |
| WO | 01/13991 | 3/2001 |
| WO | 0156521 | 8/2001 |
| WO | 02/082982 | 10/2002 |
| WO | 03070322 | 8/2003 |
| WO | 2004004412 | 1/2004 |
| WO | 2004/021885 | 3/2004 |
| WO | 2004080532 | 9/2004 |
| WO | 2005006808 | 1/2005 |
| WO | 2005122887 | 12/2005 |
| WO | 2009124035 | 10/2009 |

OTHER PUBLICATIONS

International Searching Authority, "International Search Report," issued in connection with International Patent Application No. PCT/AU2003/000804, mailed on Aug. 26, 2003 (2 pages).

International Preliminary Examining Authority, "Written Opinion," issued in connection with International Patent Application No. PCT/AU2003/000804, mailed on Oct. 16, 2003 (3 pages).

International Preliminary Examining Authority, "International Preliminary Examination Report," issued in connection with International Patent Application No. PCT/AU2003/000804, on Oct. 12, 2004 (3 pages).

International Searching Authority, "International Search Report," issued in connection with International Patent Application No. PCT/FR2003/000577, mailed on Jul. 4, 2003 (4 pages).

International Preliminary Examining Authority, "International Preliminary Examination Report," issued in connection with International Patent Application No. PCT/FR2003/000577, on May 7, 2004 (12 pages).

International Searching Authority, "International Search Report," issued in connection with International Patent Application No. PCT/US2005/021207, mailed on Feb. 8, 2006 (1 page).

The International Bureau of WIPO, "International Preliminary Report on Patentability," issued in connection with International Patent Application No. PCT/US2005/021207, on Dec. 20, 2006 (4 pages).

International Searching Authority, "International Search Report," issued in connection with International Patent Application No. PCT/US2009/038932, mailed on Jun. 5, 2009 (3 pages).

International Searching Authority, "Written Opinion," issued in connection with International Patent Application No. PCT/US2009/038932, mailed on Jun. 5, 2009 (6 pages).

Abbas et al., "Summary of Results Using the Nucleus CI24M Implant to Record the Electrically Evoked Compound Action Potential," pp. 45-59, vol. 20(1), Feb. 1999 (25 pages).

Brown et al., "Electrically Evoked Whole-Nerve Action Potentials: Data from Human Cochlear Implant Users," Acoustical Society of America, Jun. 19, 1989 (7 pages).

Diller et al., "Measurement of the Electrically Evoked Compound Action Potential Via a Neural Response Telemetry System," vol. 111, No. 5, Annals of Otology, Rhinology & Laryngology, May 2002 (8 pages).

Franck, Kevin H., "A Model of a Nucleus 24 Cochlear Implant Fitting Protocol Based on the Electrically Evoked Whole Nerve Action Potential," Ear and Hearing, 2002 (5 pages).

Lai et al., "A Simple Two-Component Model of the Electrically Evoked Compound Action Potential in the Human Cochlea," Aurology and Neuro-Otology, Nov. 2000 (13 pages).

Nicolai et al., "Performance of Automatic Recognition Algorithms in Nucleus Neural Response Telemetry (NRT)," (1 page).

Smoorenburg et al., Speech Perception in Nucleus CI24M Cochlear Implant Users with Processor Settings Based on Electrically Evoked Compound Action Potential Thresholds, Aurology and Neuro-Otology, Nov. 2002 (13 pages).

Thai-Van et al., "Modeling the Relationship Between Psychophysical Perception and Electrically Evoked Compound Action Potential Threshold in Young Cochlear Implant Recipients: Clinical Implications for Implant Fitting," International Federation of Clinical Neurophysiology, Jun. 17, 2004 (14 pages).

Riedmiller et al., "A Direct Adaptive Method for Faster Backpropagation Learning: The RPROP Algorithm," IEEE International Conference on Neural Networks, 1993 (6 pages).

International Preliminary Examining Authority, "International Preliminary Report on Patentability," issued in connection with International Patent Application No. PCT/US2009/038932, mailed on Jun. 21, 2010 (10 pages).

European Patent Office, "Supplemental European Search Report," issued in connection with European Patent Application No. 05762889.3, on May 11, 2010 (3 pages).

Brown, et al., The Relationship Between EAP and EABR Thresholds and Levels Used to Program the Nucleus 24 Speech Processor: Data from Adults, Ear and Hearing, vol. 21 (2), Apr. 2000, pp. 151-163.

Charasse, et al., "Automatic analysis of auditory nerve electrically evoked compound action potential with an artificial neural network," Artificial Intelligence in Medicine, 2004 31, 221-229.

Delgado, et al, "Automated Auditory Brainstem Response Interpretation," IEEE Engineering in Medicine and Biology, Apr./May 1994.

Charasse, et al., "Comparison of Two Different Methods to Automatically Classify Auditory Nerve Responses Recorded with NRT System," Acta Acustica United with Acustica, vol. 99 (2004) 512-519.

Seyle, et al., "Speech Perception Using Maps Based on Neural Response Telemetry Measures," Ear & Hearing, Copyright © 2002 by Lippincott Williams & Wilkins.

Vannier, et al., "Objective detection of brainstem auditory evoked potentials with a priori information from higher presentation levels," Artificial Intelligence in Medicine 25, (2002) 283-301.

Franck, et al., Estimation of Psychophysical Levels Using the Electrically Evoked Compound Action Potential Measured with the Neural Response Telemetry Capabilities of Cochlear Corporation's C124M Device, Ear & Hearing, Copyright © 2001 by Lippincott Williams & Wilkins.

Dijk, et al., "Development of a prototype fully-automated intraoperative ECAP recording tool, using NRT™ v3," Cochlear Technology Centre Europe, Mechelen, Belgium, and Laboratoire Neurosciences et Systèmes Sensoriels, Lyon France.

Hughes, et al, Comparison of EAP Thresholds with MAP Levels in the Nucleus 24 Cochlear Implant: Data from Children [Articles], Ear and Hearing, vol. 21 (2), Apr. 2000, pp. 164-174.

Abbas, et al., "Electrically Evoked Compound Action Potentials Recorded from Subjects Who Use the Nucleus C124M Device," Gantz et al. Seventh Symposium on Cochlear Implants in Children.

Baumgarte, et al., "A Nonlinear Psychoacoustic Model Applied to the ISO MPEG Layer 3 Coder," Institut für Theoretische Nachrichtentechnik und Informationsverarbeitung, Universität Hannover, Germany.

Edler, et al., "ASAC—Analysis/Synthesis Audio Codec for Very Low Bit Rates," Institut für Theoretische Nachrichtentechnik und Informationsverarbeitung, Universität Hannover, Germany.

Cohen, et al., "Spatial spread of neural excitation in cochlear implant recipients: comparison of improved ECAP method and psychophysical forward masking," Hearing Research, 179 (2003) 72-87.

Cohen, et al., "Spatial spread of neural excitation: comparison of compound action potential and forward-masking data in cochlear implant recipients," International Journal of Audiology 2004: 43: 346-355.

Miller, et al., "An Improved Method of Reducing Stimulus Artifact in the Electrically Evoked Whole-Nerve Potential," Ear & Hearing, Copyright © 2000 by Lippincott Williams & Wilkins, USA.

European Search Report, EP 01 95 9971, dated Aug. 11, 2005.

International Preliminary Examination Report, PCT/AU01/01032, dated Apr. 10, 2002.

International Search Report, PCT/AU01/01032, dated Oct. 5, 2001.

International Search Report and Written Opinion, PCT/US05/21207 dated Feb. 8, 2006.

International Preliminary Examination Report, PCT/AU02/00500, dated Dec. 12, 2003.

International Search Report, PCT/AU02/00500, dated Jun. 26, 2002.

Supplementary Partial European Search Report, EP 02 71 7863 dated Oct. 18, 2005.

Hartmann, et al., "Evoked Potentials from the Auditory Nerve Following Sinusoidal Electrical Stimulation of the Cochlea: New Possibilities for Preoperative Testing in Cochlear-Implant Candidates?" Acta Otoloaryngol (Stockh) 1994; 114, Scandinavian University Press ISSN 0001-648, pp. 495-500.

Australian Intellectual Property Office, "Examiner's First Report," issued in connection with Australian Patent Application No. 2005254100, on Dec. 17, 2009 (2 pages).

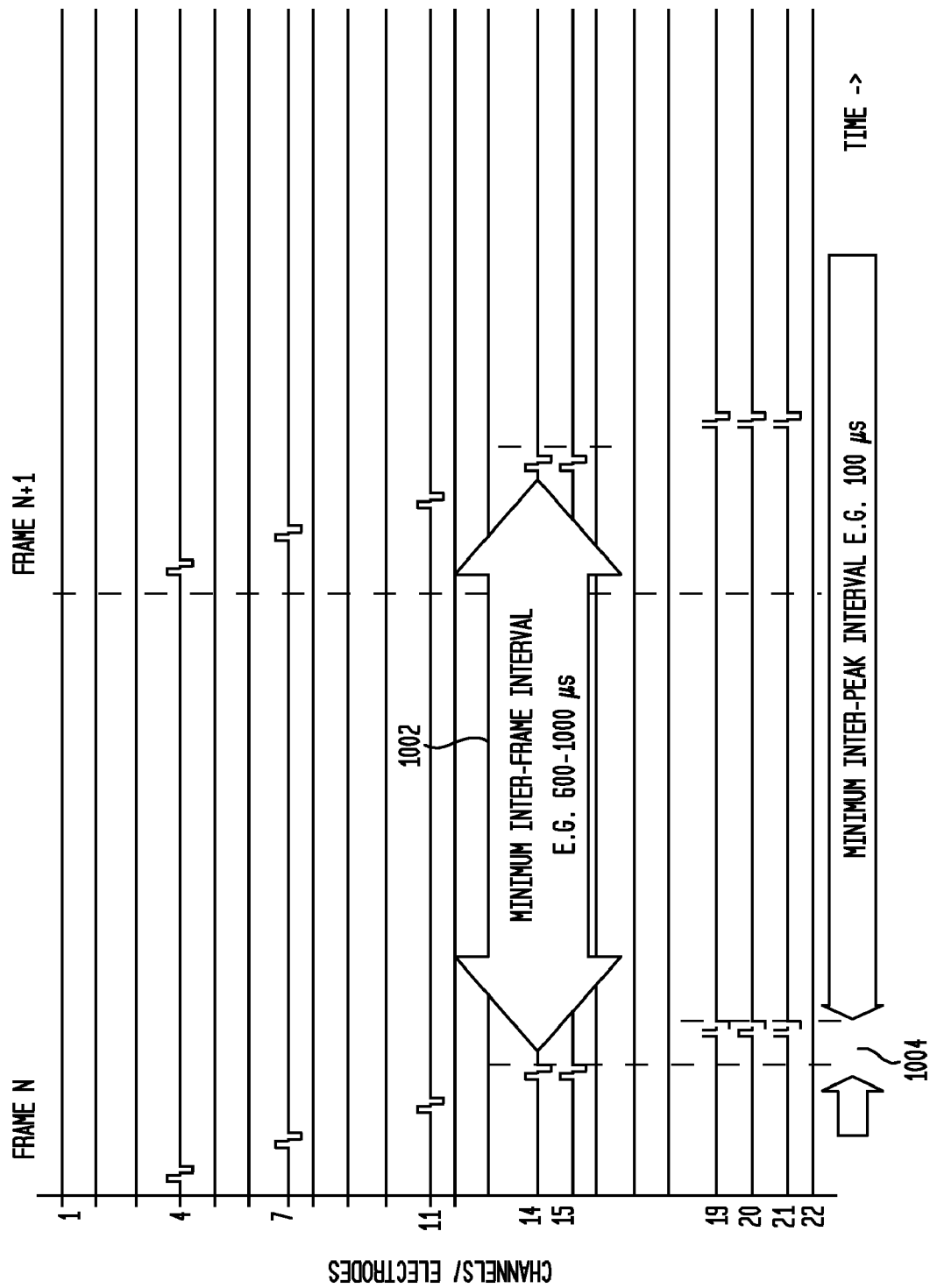

STIMULATION CHANNEL SELECTION FOR A STIMULATING MEDICAL DEVICE

BACKGROUND

1. Field of the Invention

The present invention relates generally to a stimulating medical device, and more particularly, to the selection of stimulation channels for application of stimulation by the stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of the recipient's auditory system have been developed to provide persons having sensorineural hearing loss with the ability to perceive sound. Such stimulating hearing prostheses include, for example, auditory brain stimulators and cochlear prostheses (commonly referred to as cochlear prosthetic devices, cochlear implants, cochlear devices, and the like; simply "cochlear implants" herein.) As used herein, the recipient's auditory system includes all sensory system components used to perceive a sound signal, such as hearing sensation receptors, neural pathways, including the auditory nerve and spiral ganglion, and parts of the brain used to sense sounds.

Most sensorineural hearing loss is due to the absence or destruction of the cochlear hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode different frequencies of sound.

Auditory brain stimulators are used to treat a smaller number of recipients with bilateral degeneration of the auditory nerve. For such recipients, the auditory brain stimulator provides stimulation of the cochlear nucleus in the brainstem.

In applying electrical stimulation to a recipient, medical devices, such as cochlear implants and auditory brain stimulators, typically use a coding strategy in determining the timing and intensity of the stimulation pulses to be applied to each implanted electrode contact. These coding strategies aim to divide the input signal into a number of frequency components using a different band-pass filter for each electrode. However, in order to use separate frequencies for each electrode, the filters are generally narrow and therefore rapid modulations of frequency components corresponding to periodicity in the input signal are largely removed. Periodic modulations in the input signal carry information about the sound source such as voice pitch (i.e., male or female) or the fundamental frequency for musical and other sounds. This loss of information may result in poor coding of the fundamental frequency for both speech and music. However, if wider filters are used to capture this periodic modulation, then the frequency spectrum of the signal may be less precisely characterized, which can exacerbate the overlap of current fields produced by adjacent electrodes (thereby mixing up the signals between electrodes). In addition, if these filters are too wide they could confuse periodic modulations corresponding to the fundamental frequency with those that may erroneously occur due to the combination of even-numbered lower harmonics.

SUMMARY

In one aspect of the present invention there is provided a method for delivering a stimulating signal by a stimulating medical device having a plurality of electrodes, comprising: receiving a signal; filtering the received signal to obtain a first set of one or more band-pass filtered signals; selecting a first stimulation channel corresponding to a band-pass filtered signal of the first set based on an amplitude of a corresponding band-pass filtered signal; determining if a difference between an amplitude of the band-pass filtered signal for the selected first stimulation channel and an amplitude of a band-passed filtered signal for a stimulation channel adjacent the selected stimulation channel exceeds a threshold; selecting the adjacent stimulation channel based on whether the threshold is exceeded; determining an amplitude for application of stimulation on the first stimulation channel and an amplitude for application of stimulation on the adjacent stimulation channel; and delivering a stimulation signal on the first stimulation channel and a stimulation signal on the adjacent stimulation channel in accordance with the determined amplitudes.

In another aspect there is provided an apparatus for use in delivering a stimulating signal by a stimulating medical device having a plurality of electrodes, comprising: a first filter bank configured to filter a received signal to obtain a first set of one or more band-pass filtered signals; a channel selector configured to select a first stimulation channel corresponding to a band-pass filtered signal of the first set based on an amplitude of a corresponding band-pass filtered signal, determine if a difference between an amplitude of the band-pass filtered signal for the selected first stimulation channel and an amplitude of a band-passed filtered signal for a stimulation channel adjacent the selected stimulation channel exceeds a threshold, and select the adjacent stimulation channel based on whether the threshold is exceeded; an amplitude selector configured to determine an amplitude for application of stimulation on the first stimulation channel and an amplitude for application of stimulation on the adjacent stimulation channel; and a transmitter configure to transmit a stimulation signal for delivering stimulation on the first stimulation channel and a stimulation signal for delivering stimulation on the adjacent stimulation channel in accordance with the determined amplitudes.

In yet another aspect there is provided a system for delivering a stimulating signal by a stimulating medical device having a plurality of electrodes, comprising: means for receiving a signal; means for filtering the received signal to obtain a first set of one or more band-pass filtered signals; means for selecting a first stimulation channel corresponding to a band-pass filtered signal of the first set based on an amplitude of a corresponding band-pass filtered signal; means for determining if a difference between an amplitude of the band-pass filtered signal for the selected first stimulation channel and an amplitude of a band-passed filtered signal for a stimulation channel adjacent the selected stimulation channel exceeds a threshold; means for selecting the adjacent stimulation channel based on whether the threshold is exceeded; means for determining an amplitude for application of stimulation on the first stimulation channel and an amplitude for application of stimulation on the adjacent stimulation channel; and means for delivering a stimulation signal on the first stimulation channel and a stimulation signal on the adjacent stimulation channel in accordance with the determined amplitudes.

BRIEF DESCRIPTION OF THE DRAWINGS

Embodiments of the present invention are described below with reference to the attached drawings, in which:

FIG. 10 illustrates a time interleaving scheme, in accordance with an embodiment of the invention.

DETAILED DESCRIPTION

Aspects of the present invention are generally directed to methods and systems for determining the stimulation channels for application of stimulation by a medical device, such as a cochlear implant or an auditory brain stimulator. In embodiments, the medical device filters a received signal to obtain a plurality of band-pass filtered signals, each corresponding to one or more stimulation channels. The medical device then selects a stimulation channel for application of stimulation based on the amplitudes of the band-pass filtered signals. The medical device then determines whether to apply stimulation on an adjacent stimulation channel by determining if the band-pass filtered signal corresponding to the adjacent stimulation channel has sufficient amplitude. This may be accomplished by determining if the amplitude exceeds an information limit. Next, the medical device determines whether to apply stimulation on the other adjacent channel. If the amplitudes for either adjacent channel fall below the information limit, the corresponding adjacent stimulation channel is eliminated from consideration. The medical device further may determine the amplitudes for application of stimulation on the adjacent stimulation channels, if selected, using a pitch steering function. This pitch steering function may specify a current level difference between the selected stimulation channel and the adjacent stimulation channel to use in applying the stimulation.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlear implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically and/or mechanically stimulate components of the recipient's middle or inner ear.

Figure 1:
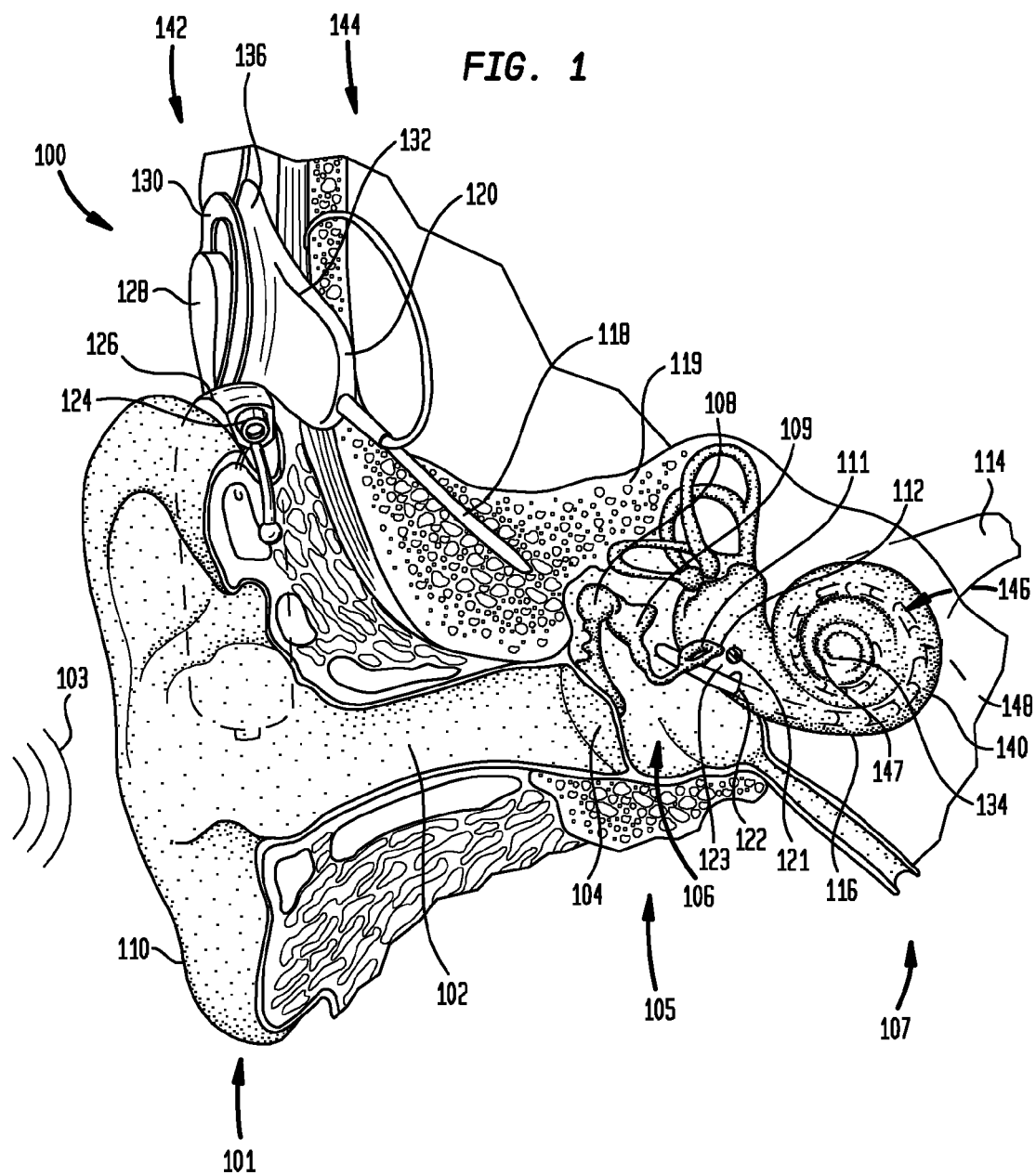
FIG. 1 is a perspective view of a cochlear implant in which embodiments of the present invention may be implemented.
Figure 2:
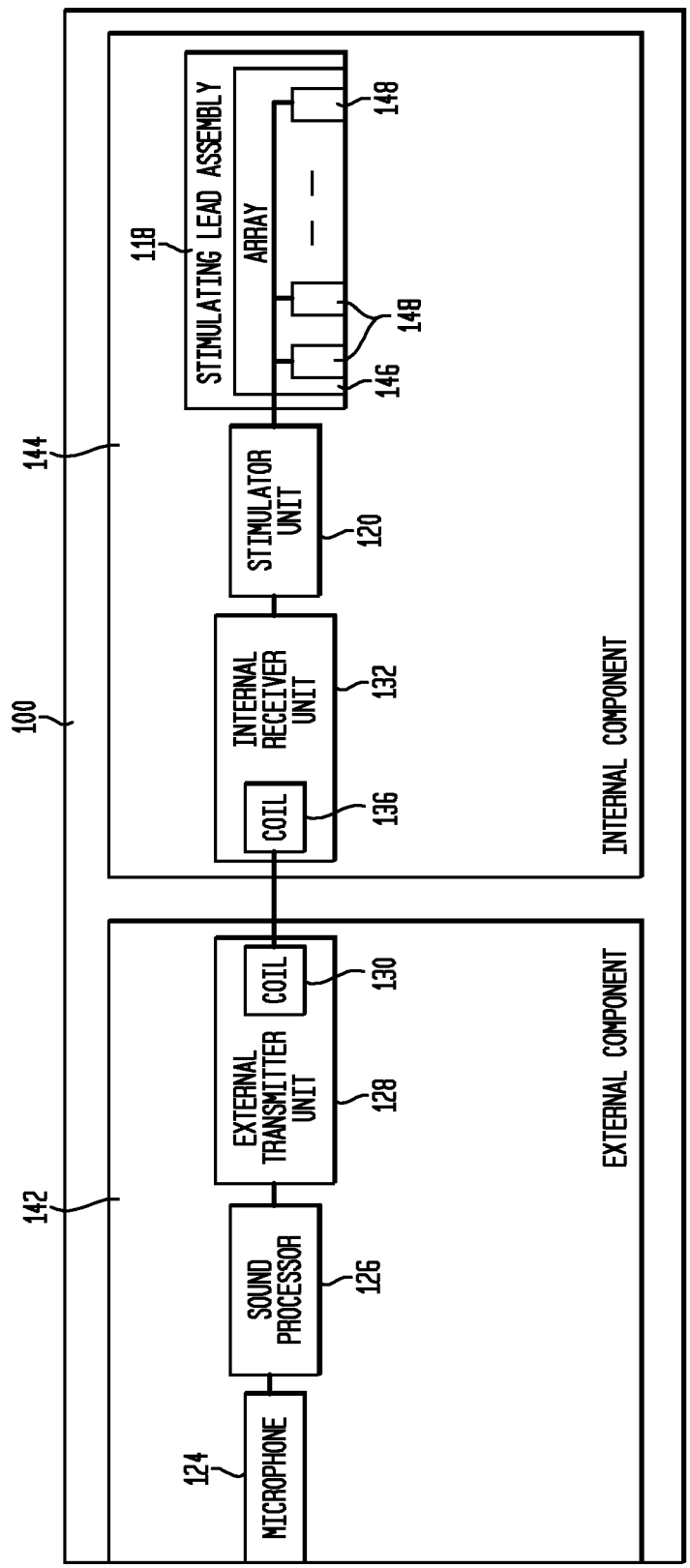
FIG. 2 is a functional block diagram of the cochlear implant of FIG. 1, in accordance with an embodiment of the present invention.

FIG. 1 is perspective view of a cochlear implant, referred to as cochlear implant 100 implanted in a recipient. FIG. 2 is a functional block diagram of cochlear implant 100. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processor 126, a power source (not shown), and an external transmitter unit 128. External transmitter unit 128 comprises an external coil 130 and, preferably, a magnet (not shown) secured directly or indirectly to external coil 130. Sound processor 126 processes the output of microphone 124 that is positioned, in the depicted embodiment, by auricle 110 of the recipient. Sound processor 126 generates encoded signals, sometimes referred to herein as encoded data signals, which are provided to external transmitter unit 128 via a cable (not shown). Sound processor 126 may further comprise a data input interface (not shown) that may be used to connect sound processor 126 to a data source, such as a personal computer or musical instrument (e.g., a MIDI instrument).

Internal component 144 comprises an internal receiver unit 132, a stimulator unit 120, and an electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130. Electrode assembly 118 has a proximal end connected to stimulator unit 120, and a distal end implanted in cochlea 140. Electrode assembly 118 extends from stimulator unit 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrode contacts 148, sometimes referred to as array of electrode contacts 146 herein. As used herein, the terms electrode contacts and electrodes are used interchangeably. Although array of electrode contacts 146 may be disposed on electrode assembly 118, in most practical applications, array of electrode contacts 146 is integrated into electrode assembly 118. As such, array of electrode contacts 146 is referred to herein as being disposed in electrode assembly 118. Stimulator unit 120 generates stimulation signals which are applied by electrode contacts 148 to cochlea 140, thereby stimulating auditory nerve 114. Because, in cochlear implant 100, electrode assembly 118 provides stimulation, electrode assembly 118 is sometimes referred to as a stimulating lead assembly.

In cochlear implant 100, external coil 130 transmits electrical signals (that is, power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient. Cochlear implant 100 may, for example, resemble a cochlear implant current used for implementing the Advanced Combination Encoder (ACE) sound coding scheme.

Figure 3:
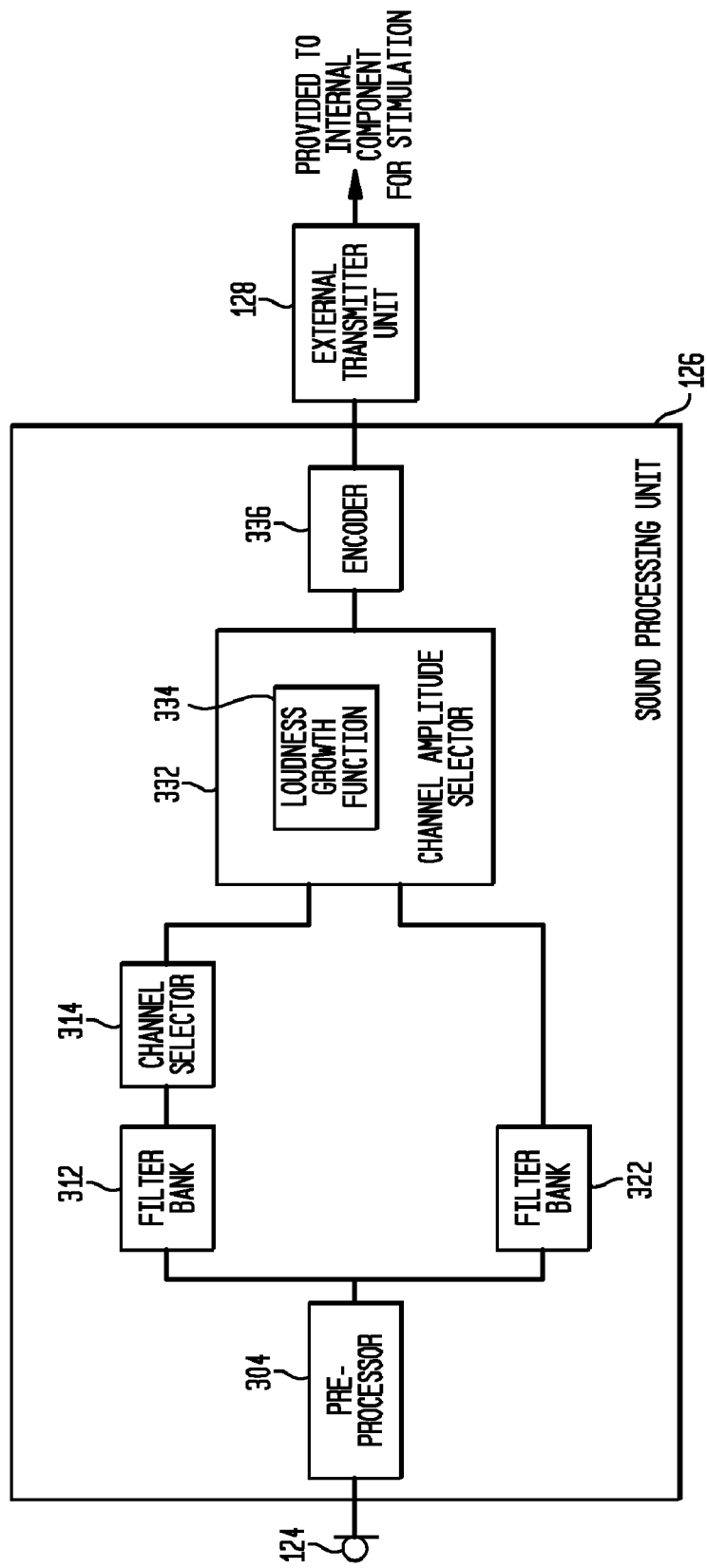
FIG. 3 illustrates a functional diagram of an exemplary sound processing unit 126, in accordance with an embodiment of the present invention.

FIG. 3 illustrates a functional diagram of an exemplary sound processing unit 126, in accordance with an embodiment. As illustrated, sound processing unit 126 receives input from one or more sound input devices, such as microphone 124. It should be appreciated, however, that any sound input device now or later developed may be used to provide one or more input sound signals. For example, in an embodiment, the sound input device may be, for example, an input jack for receiving a signal from, for example, the headphone jack of an MP3 player or other audio device.

This input is provided to a pre-processor 304. Pre-processor 304 may, for example, use a pre-emphasis filter, automatic gain control (AGC), and/or manual sensitivity control (MSC), and other signal pre-processing components. The structure and operation of audio-preprocessor 304 is considered to be well-known in the art and, therefore, is not described further herein.

After which, the signal is provided to two separate filter banks: a first filter bank 306 and a second filter bank 308. In the illustrated embodiment, filter bank 312 may comprise a set of band-pass filters with contiguous frequency boundaries, and filter bank 322 may comprise a set of broader band-pass filters with overlapping frequency boundaries.

Each filter bank 312 and 322 may output N band-pass filtered signal amplitudes, where N is the number of stimulation channels for the cochlear implant. For example, for an implant system providing 22 channels of stimulation, each filter bank may output 22 separate band-pass filtered signals, one for each stimulation channel. As will be discussed in further detail below with reference to FIG. 5, in the illustrated embodiment, the band-pass filtered signal amplitudes from filter bank 312 are used in selecting the stimulation channels for application of stimulation and the outputs of filter bank 322 are used to determine the amplitudes for the applied stimulation.

Figure 4:
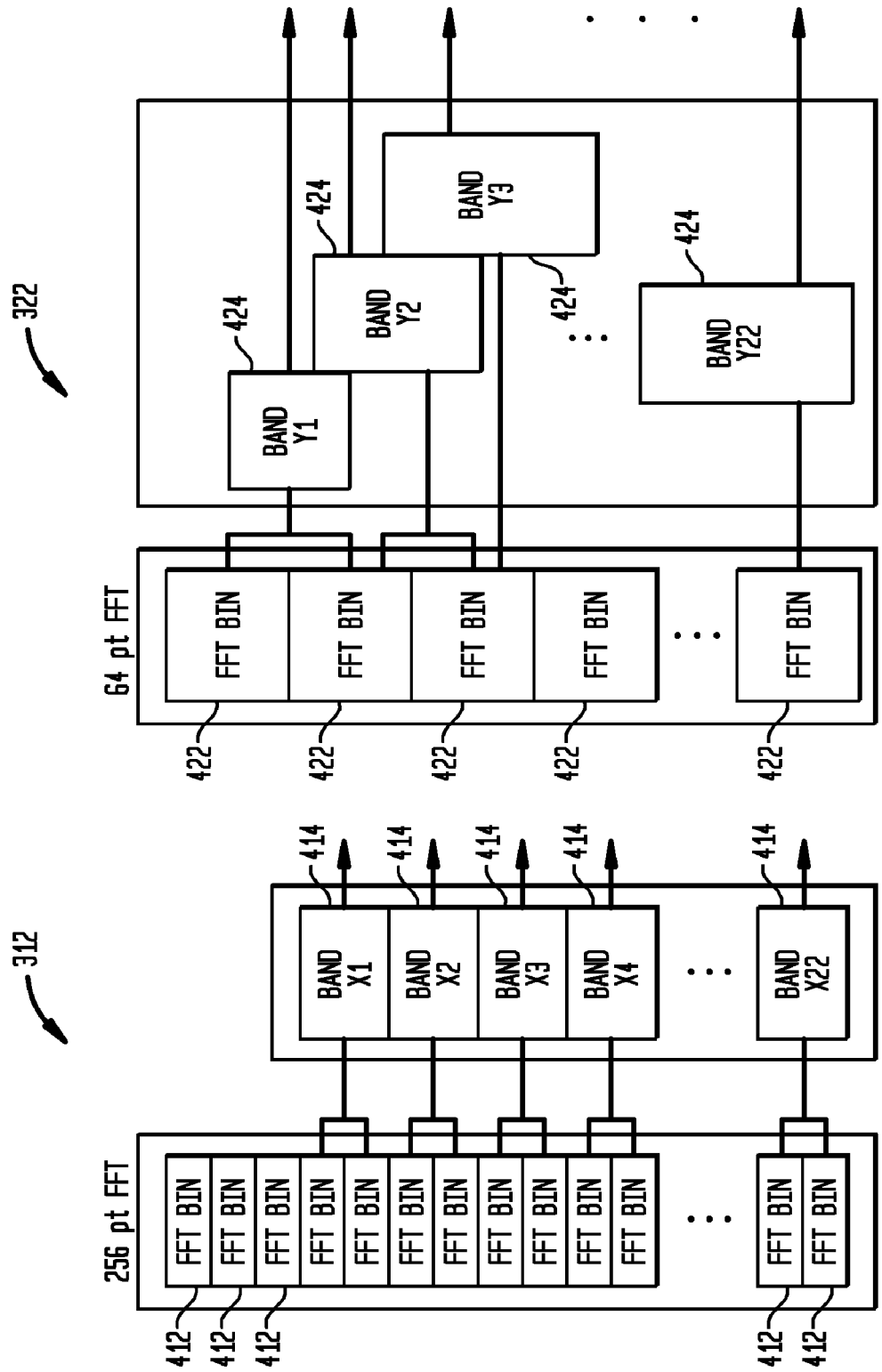
FIG. 4 provides a conceptual diagram illustrating an exemplary mechanism for implementing filter banks via a vector combination of FFT bins, in accordance with an embodiment of the present invention.

In an embodiment, a processor in sound processing unit 126 may perform two different Fast Fourier Transforms (FFTs) to construct the two filter banks 312 and 322. FIG. 4 provides a conceptual diagram illustrating an exemplary mechanism for implementing filter banks 312 and 322 via a vector combination of FFT bins. As illustrated, filter bank 312 may be implemented by a 256 point FFT that provides 256 separate FFT bins 412. Using a vector combination of FFT bins, filter bank 312 may implement a plurality (e.g., 22) of separate band-pass filters 414. In the illustrated embodiment, band-pass filters 414 have contiguous frequency boundaries. For example, in an embodiment, each of band-pass filters 414 may have a bandwidth of 125 Hz., such that, for example, the sixth band-pass filter 414 has a center frequency of 875 Hz (band-pass region of 812.5-937.5 Hz), the seventh band-pass filter 414 has a center frequency of 1000 Hz (band-pass region of 937.5-1062.5 Hz), the eighth band-pass filter 414 has a center frequency of 1125 Hz (band-pass region of 1062.5-1187.5 Hz), etc., where the frequency boundaries of each band-pass filter are contiguous. In the presently described embodiment, the bandwidth of the band-pass filter refers to the −3 dB bandwidth of the filter (i.e., portion of the frequency response of the filter that lies within 3 dB of its peak). It should be understood that the above noted center frequencies and bandwidths are exemplary, and in other embodiments the bandwidths may vary, such as for example, in a logarithmic fashion where higher frequency band-pass filters have a wider bandwidth than lower frequency band-pass filters.

FIG. 4 also conceptually illustrates filter bank 322. In the illustrated embodiment, filter bank 322 is realized by vector combination of the FFT bins 422 of a 64 point FFT. As shown, the band-pass filters 424 have a wider bandwidth and have frequency boundaries that overlap. Further, as illustrated, higher frequency band-pass filters 424 may have a wider bandwidth than lower frequency band-pass filters. In an embodiment, the bandwidths of band-pass filters 424 are from ⅔ to maximally ¾ octaves wide (or even up to, but less than, one octave wide if precise filters are used). For example, in an embodiment, the band-pass filters 424 may be 0.737 (0.737=log(5/3)/log(2)) octaves wide such that the band-pass filters 424 allow the $3^{rd}$ to $5^{th}$ harmonics of a fundamental frequency of a received sound, such as human voice, to be captured in any one band without being so wide (i.e., one octave) that "octave errors" result. For example, octave errors may result if the filters are too wide and pass amplitude modulation at the $2^{nd}$ harmonic frequency rather than at the fundamental frequency, and, for example, the fundamental frequency with $2^{nd}$ harmonic is dominant or the $2^{nd}$ and $4^{th}$ harmonics are dominant.

In an embodiment, the center frequencies of band-pass filters 424 may be the same (or approximately the same) as the center frequencies of band-pass filters 414. Further, as noted, in an embodiment, the band-pass regions of filters 424 may be sufficiently wide to pass the $3^{rd}$ and $5^{th}$ harmonics of a fundamental frequency. Thus, in an embodiment, the band-pass region of the filter 424 may be determined by assuming the center frequency of the band-pass filter passes a fundamental frequency. As such, this fundamental frequency may be assumed to be up to the center frequency divided by four. For ease of explanation, an example, will be presented where the band-pass filter 424 has a center frequency of 1000 Hz. In this example, the fundamental frequency for the $4^{th}$ harmonic centered in the band-pass filter 424 is 250 Hz, where 4*250 Hz=1000 Hz. If the band-pass filter 424 is designed to also pass the $3^{rd}$ harmonic, then the band-pass filter's lower cutoff frequency is set to 3*250 Hz, or 750 Hz. Similarly, if the upper cut-off frequency is set at the $5^{th}$ harmonic, then this upper cut-off frequency would be set to 5*250 Hz=1250 Hz. Thus, in this example, the band-pass filter 424 would have a band-pass region of 750 Hz to 1250 Hz, with a center frequency of 1000 Hz. In this example, the filter 424 is log(5/3)/log(2)=0.737 octaves wide. Or, in other words, the band-pass region of the filter 424 is approximately three-quarters of an octave wide. Further, it is noted that in this example, the band-pass filter 424 is wide enough to capture the $3^{th}$ and $5^{th}$ harmonic of a fundamental frequency, but is not so wide that it captures both a fundamental frequency and the second harmonic of a fundamental frequency. That is, there is no frequency for which both the frequency and its second harmonic would both fall within the pass-band of filter 424.

In an embodiment, the amplitudes obtained at the output of each band-pass filter 424 may be interpolated between frames to allow re-synthesis at the desired stimulation rate. For example, the stimulation rate of the cochlear implant 100 may be faster than the operation of the FFT implementing filter-bank 322. In such an embodiment, the sound processing unit 126 may calculate the amplitudes for the outputs of band-pass filters 424 for pulses between frames of the FFT by interpolation. Further, as noted above, filter bank 312 may be implemented using a more precise FFT (e.g., a 256 point FFT) than the FFT used in implementing filter bank 322 (e.g., a 64 point FFT). Using a longer FFT for filter bank 312, which is used to obtain the spectral profile, and a shorter FFT for filter bank 322, which is used to determine the instantaneous waveform amplitude, may help reduce processing latency provide greater modulation bandwidth.

In an embodiment, the amplitude outputs of band pass-filters 414 may be averaged across a number of adjacent frames to remove residual modulation in the spectral profile. This may be beneficial in stabilizing the spectral profile over a time window corresponding to the minimum period of waveform modulation desired to be detected by filter bank 312 (e.g., 60 to 80 Hz, or lower than the lowest desired fundamental frequency)

Referring back to FIG. 3, as illustrated, the band-pass filtered signal amplitudes from filter bank 312 are provided to channel selector 314, which selects the stimulation channels for which cochlear implant 100 will apply stimulation. Channel selector 314 may select the stimulation channels by examining the received band-pass filtered signals and identifying the peaks in the frequency spectrum of the received sound signal. Channel selector 314 then select the stimulation channels corresponding to these peaks. Channel selector 314 may then determine whether to also apply stimulation on channels adjacent to the selected channels based on whether the corresponding band-pass filtered signal(s) for the adjacent stimulation channels have amplitude(s) greater than an information limit. A more detailed explanation of the concept of an information limit will be discussed below with reference to FIG. 6.

Channel selector 314 provides information identifying the selected the stimulation channels on which to apply stimulation to channel amplitude selector 332. Using the band-pass filtered signal amplitudes provided by filter bank 322, channel amplitude selector 332 determines the amplitudes in terms of current levels for the stimulation channels on which stimulation is to be applied. In determining the amplitudes, channel amplitude selector 332 may apply a loudness growth function 334, which converts amplitudes in terms of dB to current levels. The selected stimulation channels and their corresponding determined current levels are provided to encoder 336, which encodes the information for transmission to the internal component 144. The encoded data is then provided to external transmitter unit 128, which transmits the encoded information to internal component 128.

Figure 5:
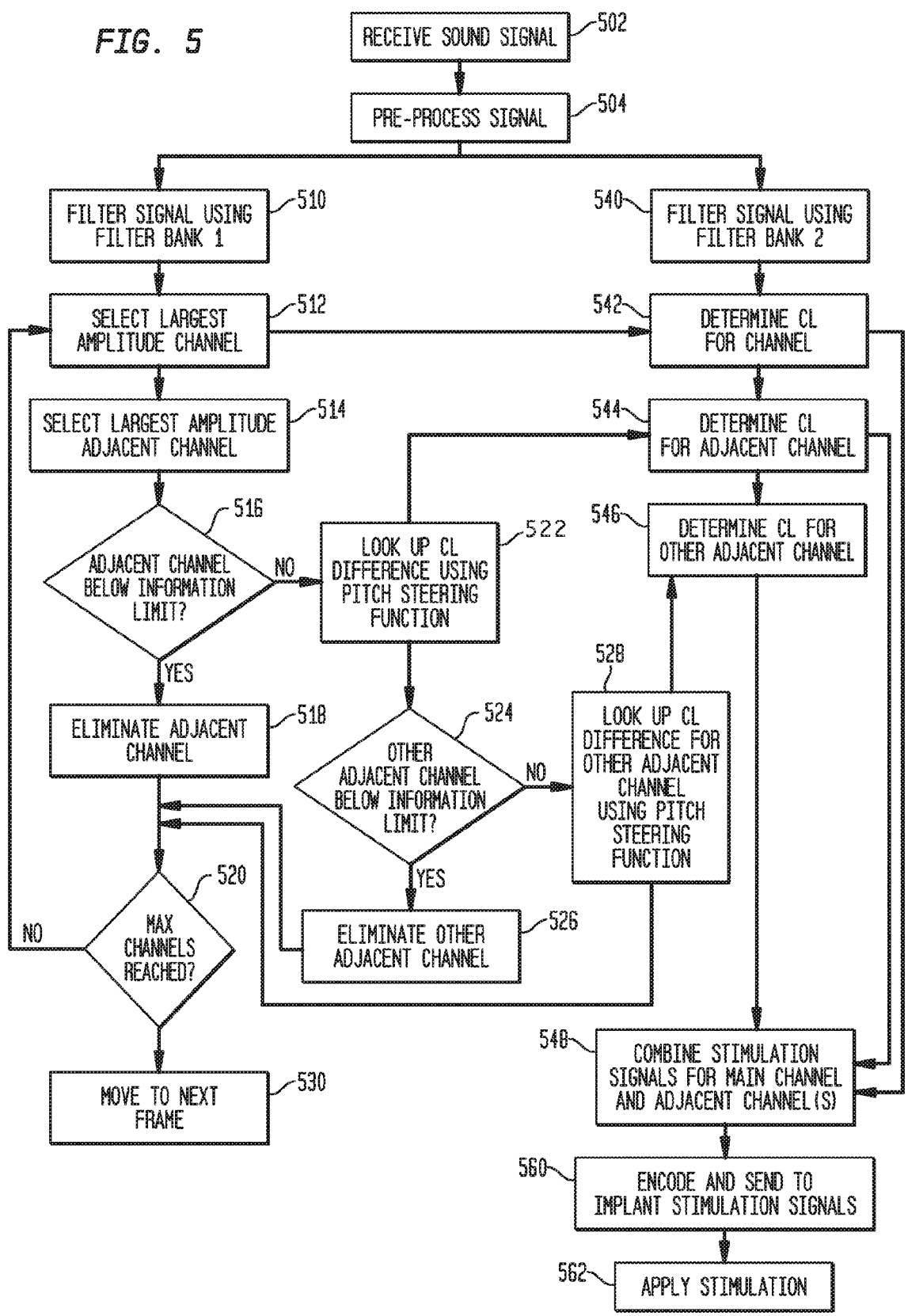
FIG. 5 provides a flow chart for selecting stimulation channels and their corresponding amplitudes, in accordance with an embodiment of the present invention.

FIG. 5 provides a flow chart for selecting stimulation channels and their corresponding amplitudes, in accordance with an embodiment. FIG. 5 will be discussed reference to the above-discussed FIG. 4. As illustrated, at block 502 a sound signal is received by microphone 124. The received sound signal is then provided to pre-processor 304 which processes, at block 504, the sound signal as discussed above and provides the processed signal to filter banks 312 and 322. Filter bank 312 filters the signal at block 510 to obtain a plurality of band-pass filtered signal amplitudes; and filter bank 322 filters the signal, at block 540, to also obtain a plurality of band-pass filtered signal amplitudes. As noted above, filter banks 312 and 322 may each provide N filtered signal amplitudes, where N is equal to the number of stimulation channels (e.g., 22) of cochlear implant 100. As illustrated in FIG. 3, filter bank 312 provides its band-pass filtered signal amplitudes to channel selector 314, and filter bank 322 provides its band-pass filtered signal amplitudes to channel amplitude selector 332.

Channel selector 314, at block 512, selects the stimulation channel corresponding to the band-pass filtered signal with the largest amplitude. Channel selector 314 then, at block 512, examines the adjacent band-pass filtered signal with the largest amplitude to determine if the amplitude of this signal falls below an information limit.

Figure 6:
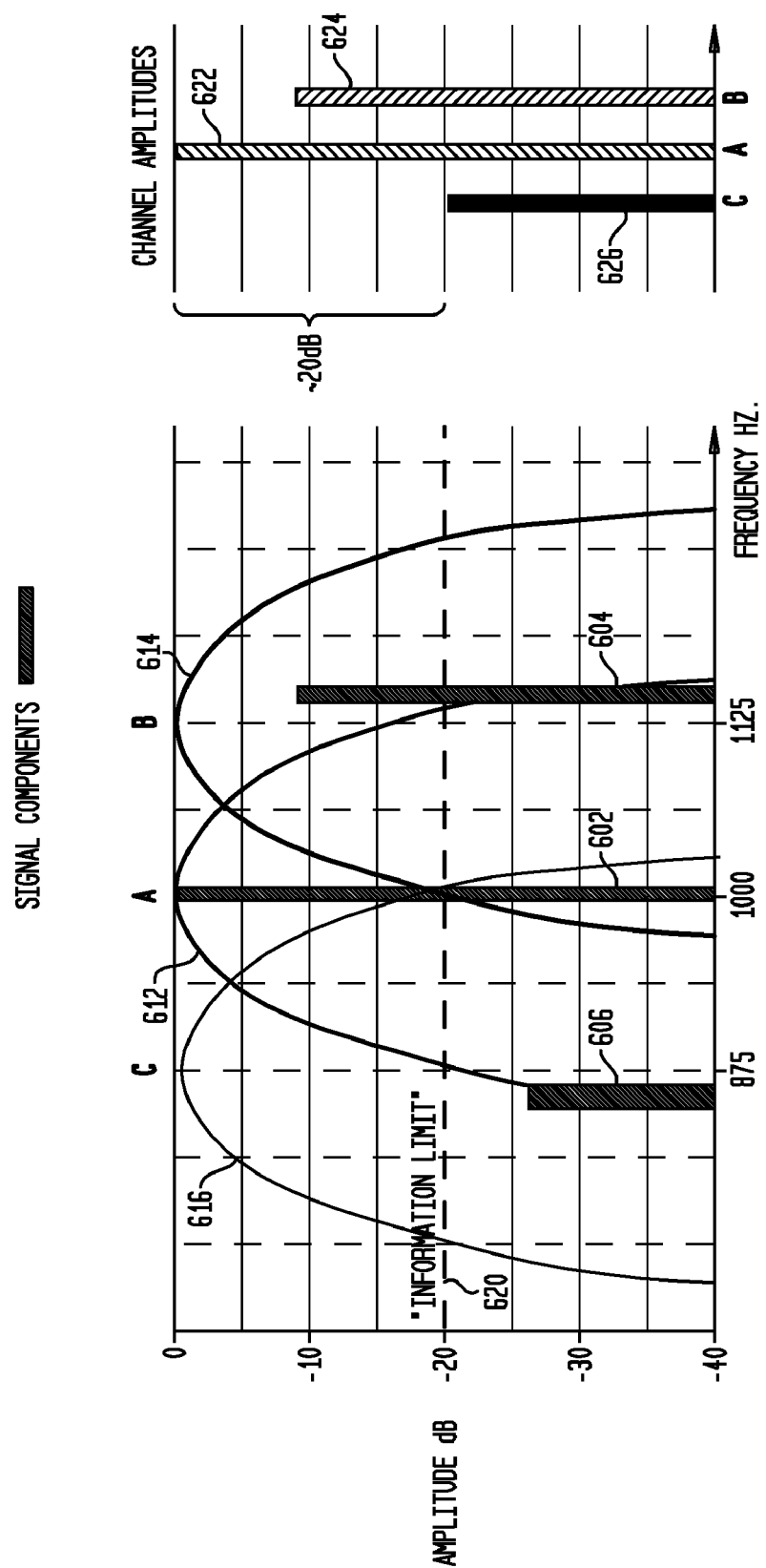
FIG. 6 illustrates components of an exemplary acoustic signal filtered by a filter bank, in accordance with an embodiment of the present invention.

FIG. 6 illustrates components of an exemplary acoustic signal filtered by a filter bank, in accordance with an embodiment. FIG. 6 will be used to explain the concept of an information limit and how the information limit may be used to save power. As shown, a filtered sound signal comprises signal components A 602, B 604, and C 606. Signal component A 602 has a normalized amplitude of 0 dB and has a frequency of 1000 Hz, signal component B 604 has a normalized amplitude of −9 dB and a frequency of 1130 Hz, and frequency component C 606 has an amplitude of −27 dB and a frequency of 870 Hz. As illustrated, frequency component A 602 is located at the center frequency of band-pass filter A, illustrated by filter A frequency response 612. Frequency component B 604 is located slightly above the center frequency of filter B, illustrated by filter B frequency response 614, and frequency component C 606 is located just below the center frequency of filter C, illustrated by filter C frequency response 616. These signal components 602, 604, and 606 may be harmonically related, such as in voiced speech.

Frequency component A 602 has the largest amplitude and is positioned in the center of filter A, and thus produces the largest output 622. The output of filter A 622, in this example, is dominated by component A 602 and is largely unaffected by the other components 604 and 606 due both to their amplitudes and the filter response 612 of filter A. The output 624 of filter B is mainly due to component B 604 and is largely unaffected by the other components 502 and 506 due to the filter response 614 of filter B. The output 626 of filter C, however, is principally due to component A 602 (centered in filter A frequency response 612) and is largely uninfluenced by component C 606 due to its low amplitude, even though it is approximately centered in filter C frequency response 616.

Also illustrated in FIG. 6, is an information limit 620. The information limit is the center-to-center rejection of adjacent filter responses. For example, as illustrated, the filter A filter response 612 is −20 dB below the filter B filter response 614 at a frequency slightly above the center frequency of filter B and below the frequency of signal component 604. This point is referred to as the information limit, because it is the minimum relative amplitude of a component in an adjacent channel that can be "seen" in the channel output on a frame by frame basis. For example, in the illustrated diagram, component C 606 is below the information limit 620 and thus is largely not seen in the output 626 of filter C, which as noted above is dominated by component A 602 centered in the neighboring filter A frequency response 612.

Referring back to FIG. 5, as noted above, channel selector 314 at block 514 determines the highest amplitude adjacent channel. Then, at block 516, channel selector 314 determines whether the highest amplitude adjacent band-pass filtered signal is below the information limit. If so, channel selector 314 eliminates the adjacent channel at block 518.

Channel selector 314 then determines, at decision 520, if the maximum number of channels, M, has been selected. For example, it may be desirable in an embodiment, to only apply stimulation on M or fewer channels. The maximum number of channels, M, may be specified by the system designer based on the particular implementation. Further, in embodiments, the maximum number of channels, M, may vary from recipient to recipient and may be adjusted after implantation of internal component 144. In an embodiment, M may be, for example, 8, 10, etc.

If the maximum number of channels, M, has been reached, channel selector 312 ends its analysis of the band-pass filtered signals for the FFT frame and progresses to analysis of the next FFT frame at block 530 (i.e., the process returns to block 510 and channel selector 312 processes the band-pass filtered signals for the next FFT frame). As used herein, the term FFT frame refers to the outputs resulting from a singular execution of the FFT (e.g., the FFT for filter bank 312).

If at decision 516 the adjacent channel has an amplitude above the information limit, channel selector 314 progresses to block 522. At block 522, channel selector 312 selects the adjacent channel and determines a current level difference between the peak amplitude signal (selected at block 512) and the adjacent channel. Channel selector 312 may use a pitch steering function in determining the current level difference. A description of an exemplary pitch steering function will be provided below with reference to FIG. 8.

Channel selector 314 then, at decision 524, examines the other adjacent band-pass filtered signal to determine if the signal falls below the information limit. If so, the other adjacent channel is eliminated at block 526 and channel selector 314 progresses to decision 520. If not, channel selector 314 progresses to block 528 and selects the adjacent channel and determines a current level difference between the peak amplitude signal (selected at block 512) and the adjacent channel. As in block 522, channel selector 312 may use a pitch steering function in determining the current level difference to use between the peak amplitude signal (selected at block 512) and the other adjacent channel. Channel selector 312 then progresses to decision 520.

If at decision 520, the maximum number of channels, M, has not been reached, channel selector 312 returns to block 512 and selects the channel with next largest peak. In these subsequent iterations, the channels previously eliminated at blocks 518 and 526 are not available for selection by channel selector 312. Channel selector 312 then continues to pass through the process (block 510 through 528) until the maximum number of channels, M, are selected. In an embodiment, channel selector 312, at block 512, may only select channels for which the corresponding band-pass filtered signal has an amplitude above a specified threshold, T-SPL. This threshold may be specified, for example, so that stimulation is not applied for channels that will have an amplitude below the threshold-level (T-level) for the stimulation channel and thus would not be perceived by the recipient. If, at decision 520, no channels are left with amplitude above the threshold, T-SPL, channel selector 312 may stop examining the current frame and progress to the next FFT frame (block 530).

Simultaneous with blocks 510-530, filter bank 322 may filter the received sound signal at block 540 and provide the filtered signals to channel amplitude selector 332. At block 542, channel amplitude selector 542 converts the amplitude (in terms of dB) of the band-pass filtered signal for the stimulation channel selected at block 512 to a current level. Channel amplitude selector 332 may use a loudness growth function in converting the amplitude in terms of dB to a corresponding current level.

At block 544, channel amplitude selector 332 may determine the amplitude (in terms) of current level for the adjacent channel using the current level difference determined at block 522, if stimulation is to be applied on the adjacent channel. That is, if the adjacent channel has not been eliminated, channel amplitude selector 332 determines the current level for the adjacent channel at block 544.

And, at block 546, channel amplitude selector 332 may determine the amplitude (in terms) of current level for the other adjacent channel using the current level difference determined at block 528, if stimulation is to be applied on the other adjacent channel (i.e., if neither the adjacent channel nor the other adjacent channel fall below the information limit). At block 548, channel amplitude selector 332 may combine the amplitude for the main channel (determined at block 542) with the amplitudes for the adjacent channel(s) (determined at blocks 544 and 546).

At block 560, the current levels for the stimulation channels on which stimulation is to be applied are provided to encoder 336. The encoder 336 then encodes the resulting information for transmission to internal component 560. Then, at block 562, stimulation in accordance with the specified current levels is applied via electrode contracts 148.

As noted above, the FFT for filter bank 312 (e.g., 256 point) may be a longer FFT than used for filter bank 322 (e.g., a 64 point FFT). Longer FFTs use a longer FFT window than shorter FFTs. Thus, using a longer FFT may increase the processing latency. In an embodiment, the shorter FFT used for filter bank 322 helps enable filter bank 322 to have a greater modulation bandwidth than filter bank 312. Because the two filter banks 312 and 322 may use FFTs of different lengths, the longer FFT may be performed less frequently than the shorter FFT. In an embodiment, the two FFTs do not operate synchronously, and the steps of 540, 542, 544, 546, 548, 560, and 562 for selection of the stimulation signal amplitudes and application of stimulation may occur more frequently than the steps 510-528 for selection of the stimulation channels. In such an embodiment, the stimulation channels used for application of stimulation in the more rapidly performed steps 540-562 may be kept the same until new stimulation channels are selected by steps 510-520. Further, in embodiments, the outputs of filter bank 322 may be interpolated between frames so that stimulation may be applied by the cochlear implant at the desired stimulation rate.

It should be understood that the above method of FIG. 5 is exemplary only and variations of the method may be used without departing from the invention. For example, in embodiments, different components and/or functional blocks may be used for performing the different steps than those discussed above. Further, in an embodiment, rather than eliminating stimulation channels from consideration, sound processing unit 126 may initially deem all stimulation channels unselected. Then, a stimulation channel remains unselected unless it is specifically selected such as, for example, at steps 512, 516, or 524.

Or, in yet another embodiment, rather than selecting up to a maximum number of stimulation channels, sound processing unit 126 may instead select up to a maximum number of peaks (e.g., groups of one or more electrodes) for application of stimulation. This may be used, for example, where simultaneous current sources are used for application of stimulation such the peak profile may be constructed using simultaneous current pulses on the groups of adjacent electrodes. Or, in yet another embodiment, pseudo-simultaneous pulses may be used to form a peak such that the inter-pulse intervals (see, e.g. FIG. 10) are shorter than the inter-peak intervals (e.g., 10-30 microseconds).

Or, in yet another embodiment, the method of FIG. 5 may be adapted to use an envelope peak, such as described in U.S. patent application Ser. No. 12/366,462, entitled "Stimulus Timing for a Stimulating Medical Device," by Zachary Smith, which is hereby incorporated by reference. In such an example, interpolation/sample rate conversion filters may be applied to the waveform amplitude envelope amplitudes between frames to provide continuous envelope samples at the original audio sampling rate. Or alternatively a time-domain filters may be used which need only be calculated when a given channel is selected for stimulation. These data may allow determination of peak positions in time for each channel. The method of FIG. 5 may be used to determine the channel peak profile from the corresponding band-pass filtered signals from filter bank 312. Thus, 1 to 3, for example, electrodes would be stimulated either simultaneously or pseudo-simultaneously synchronized to the peak in the waveform amplitude envelope. A low pass filter may be applied at the same time as re-sampling to limit the maximum pulse rate as desired (e.g., 300 Hz to limit the rate per channel to 300 pulses per second (pps)).

As noted above, at blocks 520 and 526, channel selector 314 may apply a pitch steering function in determining the current levels of stimulation to apply on adjacent channels. As used herein the term "pitch steering function" refers to any mapping or function that may be used to determine an amplitude (e.g., current level) for stimulation to be applied on a particular channel based on the amplitude (e.g., current level) of stimulation to be applied on another stimulation channel. The following provides an explanation of an exemplary pitch steering function.

In application of electrical stimulation to the cochlea, there is commonly some residual overlap of the current fields produced when stimulation is applied using adjacent electrodes 148 (FIG. 1). This is known to produce an effect in that the perceived pitch of the stimulation is steered between that when the electrodes 148 are stimulated individually. This steering can be achieved either by applying current simultaneously to adjacent electrodes or by using closely spaced sequential pulses applied via the adjacent electrodes. This phenomenon is commonly called pitch steering. The ratio between the current levels of pulses applied on the adjacent electrodes typically determines the perceived pitch in a continuous fashion.

Figure 7:
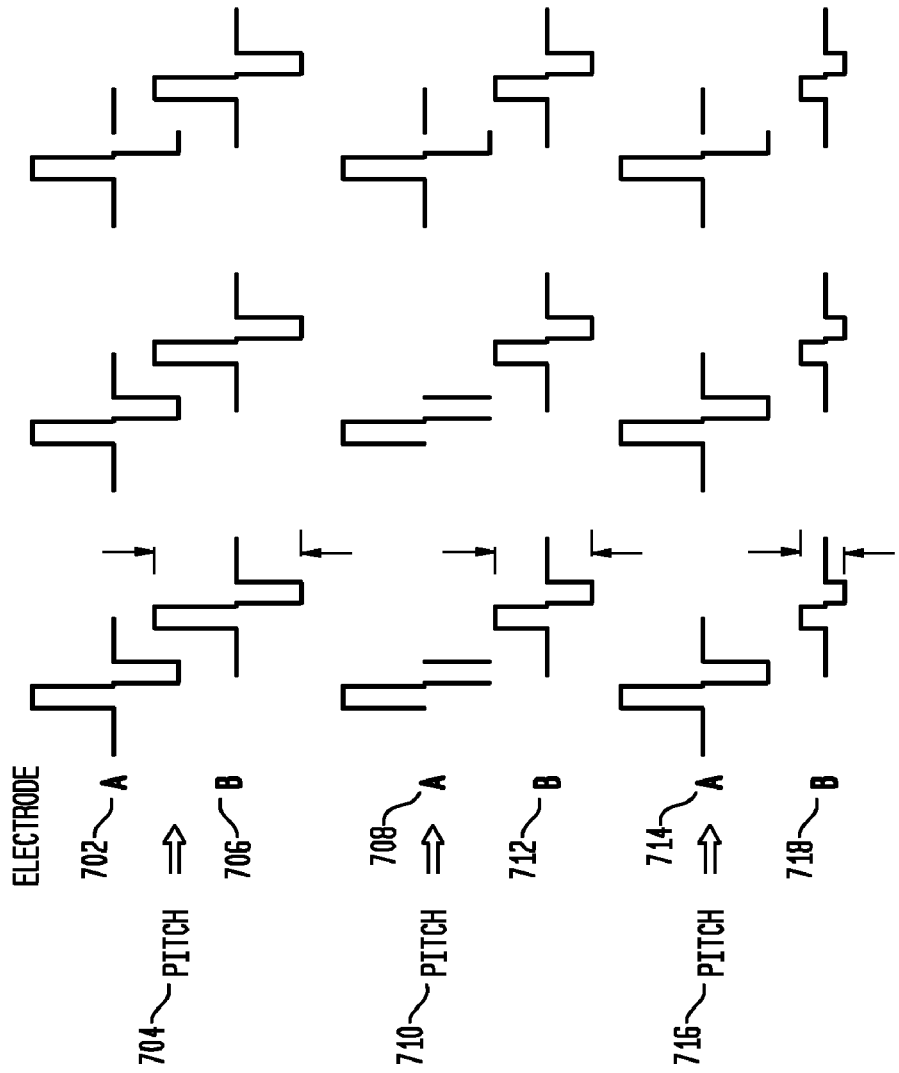
FIG. 7 provides a conceptual diagram to illustrate this concept of pitch steering, in accordance with an embodiment of the invention.

FIG. 7 provides a conceptual diagram to illustrate this concept of pitch steering. As illustrated, when stimulation 702 is applied on a first electrode (A) with a current level equal to stimulation 706 applied on an adjacent electrode (B), the resulting perceived pitch 704 may fall in the middle between the pitches that would result if stimulation was applied on each electrode individually. However, when stimulation 708 is applied on one electrode (A) with a current level slightly higher than stimulation 712 applied on an adjacent electrode (B) (e.g., by reducing the current level of stimulation applied on electrode B), the resulting perceived pitch 710 is shifted (i.e., steered) towards the frequency corresponding to the electrode (A) on which stimulation is applied with the higher current level. Further, if the difference in current levels of stimulation 714 and 718, respectively, applied on adjacent electrodes (A and B) is even greater, the resulting perceived pitch 716 moves even closer to the frequency corresponding to the electrode (A) on which the higher current level stimulation is applied. At some point, further differences in the stimulation applied on the adjacent electrodes (A and B) has no further effect on the perceived place pitch, and may result in the stimulation resulting in a perceived pitch as though stimulation was only applied on the electrode with the higher current level. The difference in stimulation levels (commonly expressed in logarithmic current level (CL) units), where there is no further change in perceived pitch is termed herein as the "pitch steering limit."

In an embodiment, the pitch steering limit is determined and used to define the minimum relative CL of stimulation applied on an adjacent electrode where this is a perceptual effect on the perceived pitch. That is, if stimulation is applied on an adjacent electrode with a CL below this pitch steering limit, there will be no perceptual effect to the user. In an embodiment, stimulation on an adjacent electrode with a CL below the pitch steering limit is not applied, thus saving power.

In an embodiment, a pitch steering function is defined that relates the relative levels of current applied to adjacent electrodes with the relative output of the band-pass filters associated with these electrodes such that the information limit derived from the filter characteristics is equated with the pitch steering limit.

Figure 8:
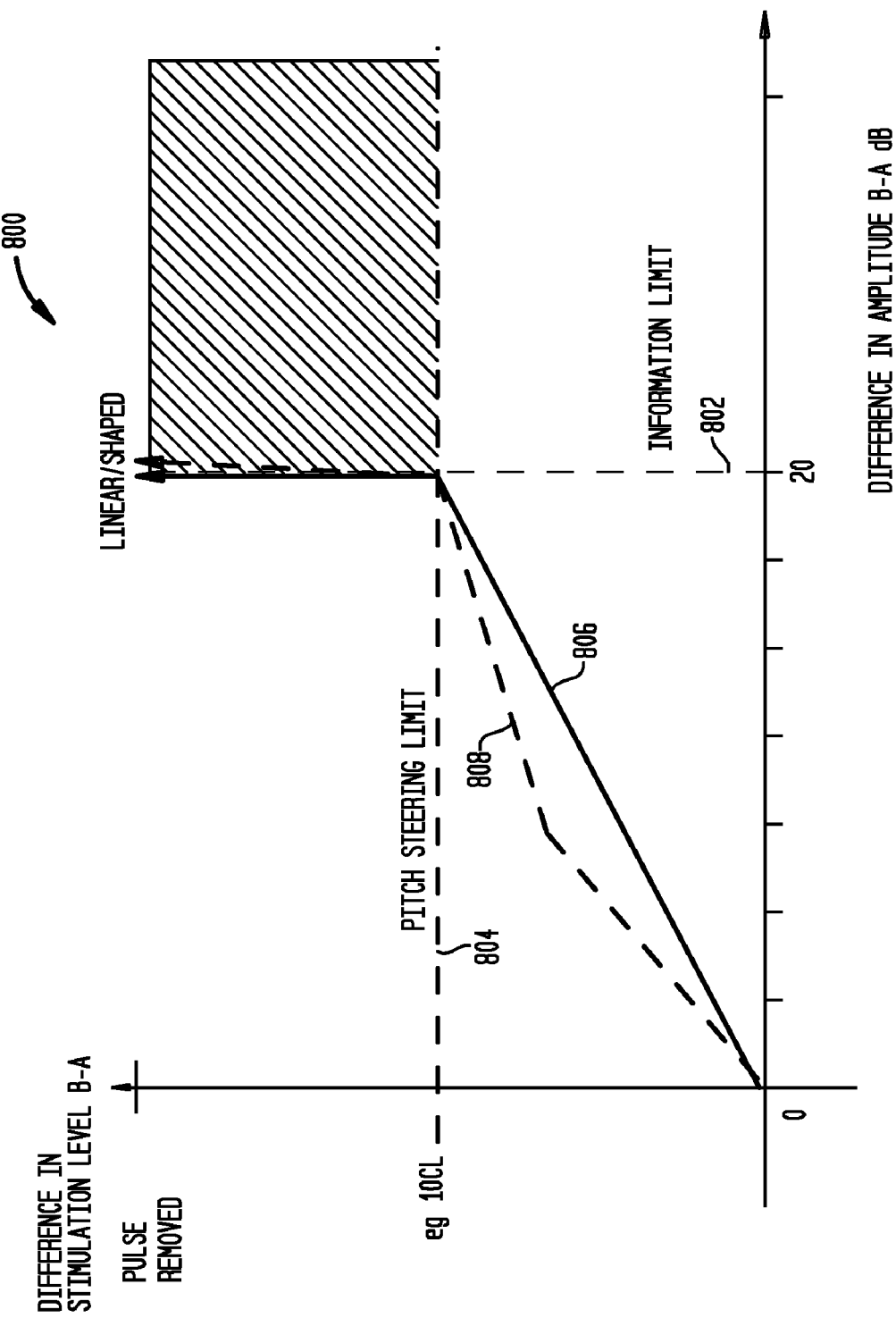
FIG. 8 provides a graph for an exemplary pitch steering function, in accordance with an embodiment of the invention.

FIG. 8 illustrates a graph 800 for an exemplary pitch steering function, in accordance with an embodiment of the invention. The X-axis of this diagram is the difference in amplitudes between the signals (e.g., the band-pass filtered signal amplitudes output from filter bank 312 of FIG. 3) for adjacent stimulation channels (A and B) in terms of dB. The Y-axis is the difference in Current Level of stimulation to be applied on the adjacent electrodes corresponding to the adjacent stimulation channels (A and B). An information limit 802 is illustrated as a vertical line on the graph at 20 dB, which in this example corresponds to the information limit discussed above with reference to FIG. 5.

Also illustrated is a pitch steering limit 804, which in this example, is a horizontal line at 10 CL. In an embodiment, a pitch steering function 806 is linearly defined as a function in which a CL difference of 0 CL is provided when the difference in amplitudes between the band-pass filtered signals (e.g., output from filter bank 312) is 0 dB; and, in which a CL of 10 CL (the pitch steering limit) is provided when the difference in amplitudes between the band-pass filtered signals is equal to 20 dB (the information limit). Above, the information limit, no stimulation is applied on the adjacent electrode, as is illustrated by the pitch steering function becoming a nearly vertical line at the information limit (20 dB). Thus, in this simple example, the pitch steering function is defined as a straight line starting at (0 CL, 0 dB) that intersects the point where the pitch steering limit is equal to the information limit and then veers vertically. Thus, in this exemplary pitch steering function, the current level varies linearly with the difference in amplitudes of the signals, but no current is applied on the adjacent electrode if either the information limit or pitch steering limit is exceeded.

FIG. 8 illustrates a curve for another pitch steering function 806. In this example, the pitch steering function also intersects 0 CL and 0 dB and the point where the pitch steering limit equals the information limit. However, in this example, the pitch steering function 806 has a steeper slope for smaller difference in signal amplitude (dB) than the slope of the pitch steering function 806 for larger differences.

In an embodiment, the slope (also referred to as gradient) of the pitch steering function may be determined in an ad hoc manner according to the Loudness Growth Function (LGF) used by the cochlear implant 100, which may be dependent on the individual cochlear implant recipient's electrical stimulation parameters, such as their threshold levels (T-levels) and maximum comfort levels (C-levels). Such a power steering function may, for example, not pass through the point where the pitch steering limit is equal to the information limit.

Figure 9:
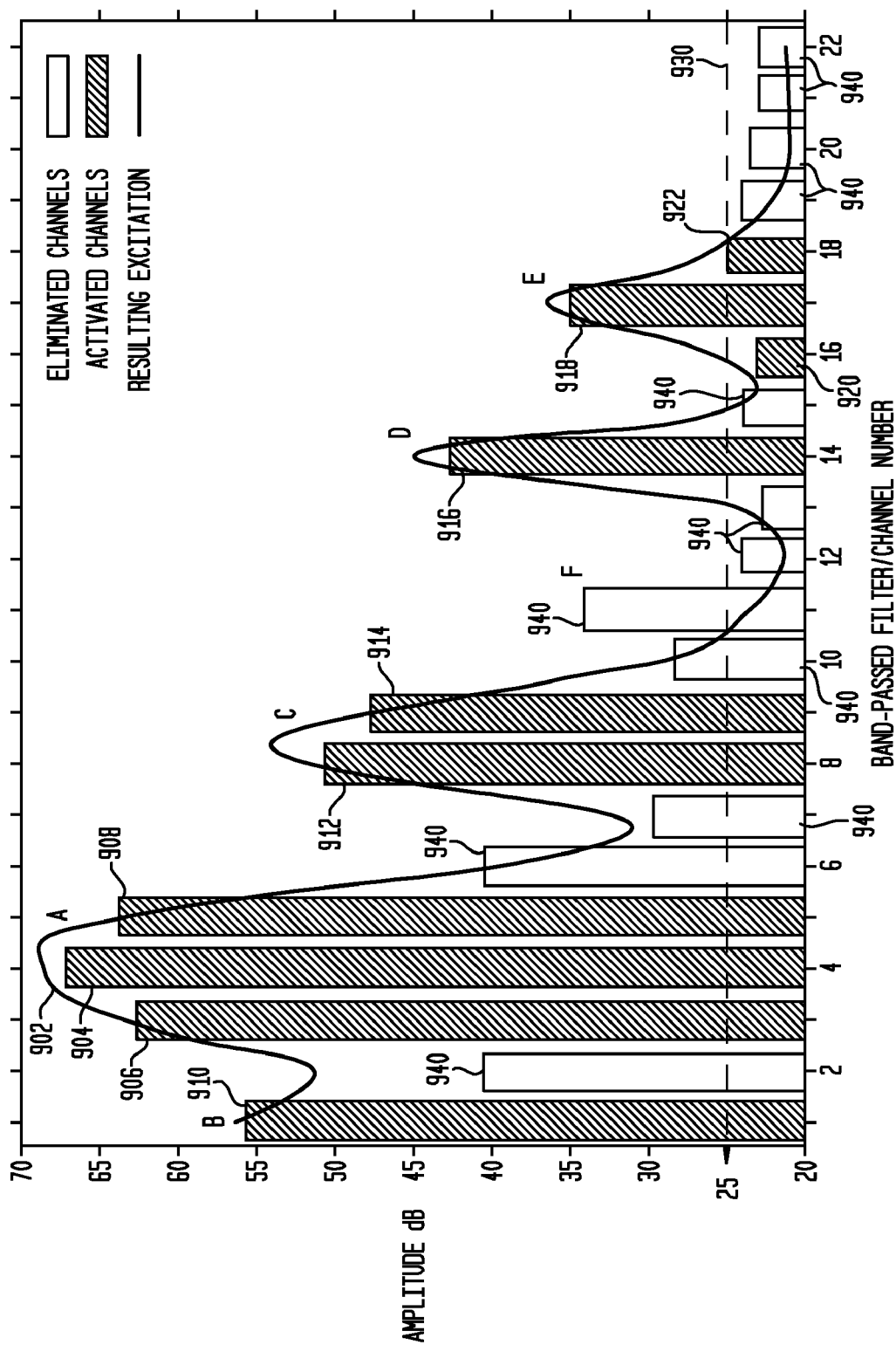
FIG. 9 illustrates amplitudes for a plurality of stimulation channels and resulting eliminated and selected stimulation channels, in accordance with an embodiment of the present invention.

FIG. 9 illustrates amplitudes for a plurality of stimulation channels and resulting eliminated and selected stimulation channels, in accordance with an embodiment. The stimulation channels in the illustrated figure are eliminated if their amplitude falls below the information limit based on the amplitude of a selected adjacent stimulation channel. These stimulation channels may be selected in accordance with the above-discussed embodiment of FIG. 5.

In the illustrated figure, the highest amplitude stimulation channel 904 (channel 4) is selected first. Then, because each of its adjacent channels 906 and 908 (channels 5 and 3, respectively) are above the information limit, they are also selected. Then, the next highest peak 910 (channel 1) is selected. Because its adjacent channel (channel 2) falls below the information limit (20 dB in this example), it is eliminated 940. The next highest peak 912 (channel 8) is then selected along with its neighboring channel 914 (channel 9) that falls above the information limit. Its other adjacent channel (channel 7) is eliminated because it falls below the information limit. Similarly, stimulation channel 916 (channel 16) is selected and its neighboring channels, which fall below the information limit (channels 14 and 17) are eliminated. Then, channel 918 (channel 17) and its neighboring channels 920 (channel 15) and 922 (channel 18) are selected. In this example, the threshold (T-SPL) 930 is selected as 25 dB, and thus all other channels are eliminated. FIG. 9 also includes a curve 902 showing the excitation resulting from the applied stimulation.

In an embodiment, the sound processing unit 126 may specify that the stimulator unit 120 apply stimulation (via electrode assembly 118) for the selected stimulation channels using a time interleaving mechanism to avoid substantial interactions either between channels or within channels. FIG. 10 illustrates a time interleaving scheme, in accordance with an embodiment of the invention. As shown, stimulation is applied on channels 4, 7, 11, adjacent channels 14 and 15, and adjacent channels 19, 20, and 21. As shown, the stimulation is applied using bi-phasic pulses. As shown, pulses on a particular stimulation channel are applied such that there is a minimum inter-frame interval 1002 of approximately 600 to 1000 micro-seconds. This minimum time for application of stimulation on a particular may be, for example, a time greater than or equal to the refractive period for the primary auditory nerve fibers that will be stimulated in order to remove potential interactions between subsequent pulses. This inter-frame interval may be varied according to the individual user's neural characteristics.

Also, as illustrated, stimulation on adjacent pulses is applied simultaneously or nearly simultaneously. In addition, the cochlear implant may also use a minimum inter-peak interval 1004 that may have a value of approximately 100 microseconds. This minimum inter-peak interval specifies the minimum time separation between pulses applied on a particular electrode (or group of adjacent electrodes) and subsequent stimulation applied on another electrode (or group of adjacent electrodes). The value of the minimum inter-peak interval may be selected to reduce interactions between the stimulation applied via these groups of one or more electrodes.

Although the above discussed embodiments were discussed with reference to two FFT filter banks 312 and 322 providing the two different band-pass filter banks, in another embodiment a single FFT may be used for providing both sets of band-pass filtered signals. Further, in yet another embodiment, rather than employing an FFT, time domain filters (e.g., FIR or IIR) filters may be used to construct the two filter banks. This may involve, for example, obtaining the amplitude envelopes of pairs of phase quadrature filters for each of each filter bank. Or, for example, in an embodiment, an FFT may be used to provide one filter bank (e.g., filter bank 312) and time-domain filters may be used to provide the other filter bank (e.g., filter bank 322).

In various implementations of the subject matter described, such as the embodiment of FIG. 3, components may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, firmware, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for delivering a stimulating signal by a stimulating medical device having a plurality of electrodes, comprising:
   receiving a signal;
   filtering the received signal to obtain a first set of one or more band-pass filtered signals;
   selecting a first stimulation channel corresponding to a band-pass filtered signal of the first set based on an amplitude of the corresponding band-pass filtered signal;
   determining if a difference between an amplitude of the band-pass filtered signal for the selected first stimulation channel and an amplitude of a band-passed filtered signal for a stimulation channel adjacent the selected stimulation channel exceeds a threshold;
   selecting the adjacent stimulation channel based on whether the threshold is exceeded;
   determining an amplitude for application of stimulation on the first stimulation channel and an amplitude for application of stimulation on the adjacent stimulation channel; and
   delivering a stimulation signal on the first stimulation channel and a stimulation signal on the adjacent stimulation channel in accordance with the determined amplitudes.

2. The method of claim 1, further comprising:
   determining if a difference between the amplitude of the band-pass filtered signal for the selected first stimulation channel and the amplitude of a band-passed filtered signal for an other stimulation channel adjacent the selected stimulation channel exceeds a threshold;
   selecting the other adjacent stimulation channel based on whether the threshold is exceeded;
   determining an amplitude for application of stimulation on the other stimulation channel; and
   delivering a stimulation signal on the other stimulation channel in accordance with the determined amplitude for the other stimulation channel.

3. The method of claim 2, further comprising:
   iteratively performing the steps of selecting a first stimulation channel, determining if a difference in amplitude exceeds a threshold, selecting the adjacent channel, and determining amplitudes for application of stimulation exceeds a threshold; and
   eliminating the adjacent channel from consideration in subsequent iterations if the threshold is not exceeded.

4. The method of claim 3, wherein the step of iteratively performing the steps is performed until a maximum number of first stimulation channels are selected or no stimulation channels that have not been selected or eliminated remain for which an amplitude of the corresponding band-pass filtered signal exceeds a threshold.

5. The method of claim 1, wherein the threshold is an information limit; and
   wherein selecting the adjacent stimulation channel comprises selecting the adjacent stimulation channel if the difference is less than the information limit.

6. The method of claim 5, wherein the information limit is set in accordance with a center to center rejection of filter responses for filtering the band-pass filtered signal for the first stimulation channel and the band-pass filtered signal for the adjacent stimulation channel.

7. The method of claim 1, wherein the determining of the amplitude for application of stimulation on the first stimulation channel and of the amplitude for application of stimulation on the adjacent stimulation channel, comprises:
   determining the amplitude for application of stimulation on the adjacent stimulation channel in accordance with a pitch steering function.

8. The method of claim 7, wherein the pitch steering function specifies a difference in amplitude for application of stimulation on the adjacent stimulation channel based on the amplitude for application of stimulation on the first stimulation channel.

9. The method of claim 8, wherein the pitch steering function specifies that the difference in amplitude is equal to a pitch steering limit when the difference in amplitudes between the band-pass filtered signals corresponding to the first stimulation channel and the adjacent stimulation channel is equal to an information limit; and
   wherein the information limit is set in accordance with a center to center rejection of filter responses for filtering the band-pass filtered signal for the first stimulation channel and the band-pass filtered signal for the adjacent stimulation channel; and
   wherein the pitch steering limit is set in accordance with the difference in amplitudes for application of stimulation on the first stimulation channel and the adjacent stimulation channel at which a recipient of the stimulating medical devices perceives no change in perceived pitch when stimulation is applied on the first stimulation channel and the adjacent stimulation channel and the amplitudes for application of stimulation on the adjacent channel are varied.

10. The method of claim 1, further comprising:
    filtering the signal to obtain a second set of one or more band-pass filtered signals; and
    wherein determining an amplitude for application of stimulation on the first stimulation channel comprises:
    determining the amplitude using at least one of the band-pass filtered signals from the second set.

11. The method of claim 10, wherein each of the band-pass filtered signals of the first set corresponds to at least one band-pass filtered signal in the second set.

12. The method of claim 11, wherein the corresponding band-pass filtered signals in the first and second sets correspond to particular stimulation channels, respectively, for delivering stimulation signals using the stimulating medical device.

13. The method of claim 12, wherein each particular channel corresponds to one or more of the electrodes for use in delivering a stimulating signal for the channel.

14. The method of claim 10, wherein filtering the signal to obtain a second set of one or more band-pass filtered signals comprises:
    filtering the signal using a set of band-pass filters, wherein at least one of the filters has a band-pass region sufficiently wide to pass a third and fifth harmonic of a fundamental frequency but not so wide as to pass the fundamental frequency and a second harmonic of the fundamental frequency.

15. The method of claim 14, wherein the band-pass region is approximately three-quarters of an octave wide.

16. The method of claim 1, wherein the stimulating medical device is a cochlear implant.

17. An apparatus for use in delivering a stimulating signal by a stimulating medical device having a plurality of electrodes, comprising:
a first filter bank configured to filter a received signal to obtain a first set of one or more band-pass filtered signals;
a channel selector configured to select a first stimulation channel corresponding to a band-pass filtered signal of the first set based on an amplitude of the corresponding band-pass filtered signal, determine if a difference between an amplitude of the band-pass filtered signal for the selected first stimulation channel and an amplitude of a band-passed filtered signal for a stimulation channel adjacent the selected stimulation channel exceeds a threshold, and select the adjacent stimulation channel based on whether the threshold is exceeded;
an amplitude selector configured to determine an amplitude for application of stimulation on the first stimulation channel and an amplitude for application of stimulation on the adjacent stimulation channel; and
a transmitter configure to transmit a stimulation signal for delivering stimulation on the first stimulation channel and a stimulation signal for delivering stimulation on the adjacent stimulation channel in accordance with the determined amplitudes.

18. The apparatus of claim 17, wherein the channel selector is further configured to determine if a difference between the amplitude of the band-pass filtered signal for the selected first stimulation channel and an amplitude of a band-passed filtered signal for an other stimulation channel adjacent the selected stimulation channel exceeds a threshold, select the other adjacent stimulation channel based on whether the threshold is exceeded; and wherein the amplitude selector is further configured to determine an amplitude for application of stimulation on the other stimulation channel; and wherein the transmitter is further configured to transmit a stimulation signal for application of stimulation on the other stimulation channel in accordance with the determined amplitude for the other stimulation channel.

19. The apparatus of claim 18, wherein the channel selector and amplitude selector are configured to iteratively perform the steps of selecting a first stimulation channel, determining if a difference in amplitude exceeds a threshold, selecting the adjacent channel, and determining amplitudes for application of stimulation exceeds a threshold; and wherein the channel selector is configured to eliminate the adjacent channel from consideration in subsequent iterations if the threshold is not exceeded.

20. The apparatus of claim 19, wherein the channel and amplitude selectors are configured to iteratively perform the steps until a maximum number of first stimulation channels are selected or no stimulation channels that have not been selected or eliminated remain for which an amplitude of the corresponding band-pass filtered signal exceeds a threshold.

21. The apparatus of claim 17, wherein the threshold is an information limit; and
wherein the channel selector is configured to select the adjacent stimulation channel by selecting the adjacent stimulation channel if the difference is less than the information limit.

22. The apparatus of claim 21, wherein the information limit is set in accordance with a center to center rejection of filter responses for filtering the band-pass filtered signal for the first stimulation channel and the band-pass filtered signal for the adjacent stimulation channel.

23. The apparatus of claim 17, wherein at least one of the channel selector and the amplitude selector are configured to determine the amplitude for application of stimulation on the first stimulation channel and the amplitude for application of stimulation on the adjacent stimulation channel by being further configured to determine the amplitude for application of stimulation on the adjacent stimulation channel in accordance with a pitch steering function.

24. The apparatus of claim 23, wherein the pitch steering function specifies a difference in amplitude for application of stimulation on the adjacent stimulation channel based on the amplitude for application of stimulation on the first stimulation channel.

25. The apparatus of claim 24, wherein the pitch steering function specifies that the difference in amplitude is equal to a pitch steering limit when the difference in amplitudes between the band-pass filtered signals corresponding to the first stimulation channel and the adjacent stimulation channel is equal to an information limit; and
wherein the information limit is set in accordance with a center to center rejection of filter responses for filtering the band-pass filtered signal for the first stimulation channel and the band-pass filtered signal for the adjacent stimulation channel; and
wherein the pitch steering limit is set in accordance with the difference in amplitudes for application of stimulation on the first stimulation channel and the adjacent stimulation channel at which a recipient of the stimulating medical devices perceives no change in perceived pitch when stimulation is applied on the first stimulation channel and the adjacent stimulation channel and the amplitudes for application of stimulation on the adjacent channel are varied.

26. The apparatus of claim 17, further comprising:
a second filter bank configured to filter the signal to obtain a second set of one or more band-pass filtered signals; and
wherein the amplitude selector is configured to determine an amplitude for application of stimulation on the first stimulation channel by determining the amplitude using at least one of the band-pass filtered signals from the second set.

27. The apparatus of claim 26, wherein each of the band-pass filtered signals of the first set corresponds to at least one band-pass filtered signal in the second set.

28. The apparatus of claim 27, wherein the corresponding band-pass filtered signals in the first and second sets correspond to particular stimulation channels, respectively, for delivering stimulation signals using the stimulating medical device.

29. The apparatus of claim 28, wherein each particular channel corresponds to one or more of the electrodes for use in delivering a stimulating signal for the channel.

30. The apparatus of claim 26, wherein the second filter bank comprises:
at least one band-pass filter having a band-pass region sufficiently wide to pass a third and fifth harmonic of a fundamental frequency but not so wide as to pass the fundamental frequency and a second harmonic of the fundamental frequency.

31. The apparatus of claim 30, wherein the band-pass region is approximately three-quarters of an octave wide.

32. The apparatus of claim 17, wherein the first filter bank is realized using a fast fourier transform.

33. The apparatus of claim 17, wherein the stimulating medical device is a cochlear implant.

34. A system for delivering a stimulating signal by a stimulating medical device having a plurality of electrodes, comprising:
- means for receiving a signal;
- means for filtering the received signal to obtain a first set of one or more band-pass filtered signals;
- means for selecting a first stimulation channel corresponding to a band-pass filtered signal of the first set based on an amplitude of the corresponding band-pass filtered signal;
- means for determining if a difference between an amplitude of the band-pass filtered signal for the selected first stimulation channel and an amplitude of a band-passed filtered signal for a stimulation channel adjacent the selected stimulation channel exceeds a threshold;
- means for selecting the adjacent stimulation channel based on whether the threshold is exceeded;
- means for determining an amplitude for application of stimulation on the first stimulation channel and an amplitude for application of stimulation on the adjacent stimulation channel; and
- means for delivering a stimulation signal on the first stimulation channel and a stimulation signal on the adjacent stimulation channel in accordance with the determined amplitudes.

* * * * *